(12) United States Patent
Brown et al.

(10) Patent No.: US 7,982,105 B2
(45) Date of Patent: Jul. 19, 2011

(54) TRANSGENIC CORN SEED WITH ENHANCED FREE LYSINE

(75) Inventors: Wayne E. Brown, St. Charles, MO (US); Shihshieh Huang, Woodland, CA (US); Thomas M. Malvar, North Stonington, CT (US)

(73) Assignee: Monsanto Technology LLC, St. Louis, MO (US)

( * ) Notice: Subject to any disclaimer, the term of this patent is extended or adjusted under 35 U.S.C. 154(b) by 512 days.

(21) Appl. No.: 11/513,543

(22) Filed: Aug. 31, 2006

(65) Prior Publication Data

US 2007/0192896 A1 Aug. 16, 2007

Related U.S. Application Data

(63) Continuation-in-part of application No. 11/311,892, filed on Dec. 19, 2005, now abandoned, and a continuation-in-part of application No. 11/394,567, filed on Mar. 31, 2006, now abandoned.

(51) Int. Cl.
*A01H 5/10* (2006.01)
*C12N 15/00* (2006.01)

(52) U.S. Cl. .................. 800/320.1; 800/298; 435/320.1

(58) Field of Classification Search .................. None
See application file for complete search history.

(56) References Cited

U.S. PATENT DOCUMENTS

| | | |
|---|---|---|
| 6,326,193 B1 | 12/2001 | Liu |
| 7,713,735 B2 | 5/2010 | Rommens |
| 2002/0137710 A1 | 9/2002 | Liu |
| 2002/0182223 A1 | 12/2002 | LaCount |
| 2005/0005330 A1 | 1/2005 | Falco |
| 2005/0176670 A1 | 8/2005 | Huang |
| 2005/0193444 A1 | 9/2005 | Malvar |
| 2006/0041957 A1 | 2/2006 | McGonigle |
| 2006/0156428 A1 | 7/2006 | Rommens et al. |

FOREIGN PATENT DOCUMENTS

| | | |
|---|---|---|
| WO | WO 01/88121 A1 | 11/2001 |
| WO | WO 2004/022777 A1 | 3/2004 |

OTHER PUBLICATIONS

Zhu et al., Plant Physiol. 2004, vol. 135, pp. 129-136.*
International Search Report, PCT/US06/41439, Mar. 19, 2007, Monsanto Technology, LLC.
Edson L. Kemper, The Role of Opaque2 . . . , The Plant Cell, vol. 11, Oct. 1999,p. 1981-1993 (see pp. 1982, 1986-1989).
Stepansky A., Lysine Catabolism, an Effective Versatile Regulator . . . , Amino Acids, 2006, vol. 30, p. 121-125 (see whole document).
Horsch R.B., A simple and General Method for Transferring Genes into Plants, Science, Mar. 8, 1985, vol. 227, p. 1229-1231 (see p. 1229).
Appendix D-2 ("Characterization of the Inserted FLAVR SAVR and kanr Genes by Southern Blot Analysis". pp. 116-153 in: Redenbaugh et al. Safety Assessment of Genetically Engineered Fruits and Vegetables, CRC Press, 1992.
U.S. Appl. No. 11/311,892, filed Dec. 19, 2005, Shihshieh Huang.
U.S. Appl. No. 11/394,567, filed Mar. 31, 2006, Shihshieh Huang.
Extended European Search Report dated Jan. 8, 2009 (EP Appl. No. 067402149).
Non-final office action for U.S. Appl. No. 11/394,567 mailed Mar. 30, 2009.
Final office action for U.S. Appl. No. 11/311,892 mailed Nov. 25, 2008.
EP 06740214.9—Extended European Search Report—dated Jan. 8, 2009.
PCT/US06/11946—International Search Report—dated Dec. 12, 2006.
PCT/US06/41439—International Search Report—dated Mar. 19, 2007.

* cited by examiner

*Primary Examiner* — Ashwin Mehta
(74) *Attorney, Agent, or Firm* — Schwegman, Lundberg & Woessner, P.A.

(57) ABSTRACT

Transgenic corn seed with high levels of free lysine resulting from a recombinant DNA construct having an endosperm specific promoter and an embryo specific promoter operably linked to gene suppression elements for suppressing the production of an endogenous lysine catabolite.

6 Claims, 2 Drawing Sheets

TRANSGENIC CORN SEED WITH ENHANCED FREE LYSINE

REFERENCE TO RELATED APPLICATIONS [FOR US]

This application is a Continuation-In-Part of U.S. patent application Ser. Nos. 11/311,892, filed 19 Dec. 2005, now abandoned and Ser. No. 11/394,567, filed 31 Mar. 2006, now abandoned incorporated herein by reference.

INCORPORATION OF SEQUENCE LISTING

A computer readable form (CRF) of the sequence listing on CD-R, containing the text file named 38-21(53489)D_SeqListing.txt, which is 37 KB (measured in MS-WINDOWS), was created on Aug. 31, 2006 and is herein incorporated by reference.

FIELD OF THE INVENTION

Disclosed herein are transgenic corn seeds with enhanced levels of free lysine resulting from recombinant DNA in transgenic corn cells and methods of making and using such seeds.

BACKGROUND

Dizigan et al. disclose in US 2005/0132437 A1, now U.S. Pat. No. 7,157,281, high lysine corn compositions having recombinant DNA expressing dihydropicolinic acid synthase which is useful as nutritionally-enhanced animal feed.

SUMMARY OF THE INVENTION

This invention provides transgenic corn seed having at least 1300 ppm free lysine, e.g. between 1300 and 4000 ppm free lysine, resulting from expression of recombinant DNA in transgenic corn cells comprising an embryo specific promoter operably linked to DNA for suppressing production of the endogenous LKR-SDH protein and an endosperm specific promoter operably linked to DNA for suppressing production of the endogenous LKR-SDH protein. In an embodiment of the invention the transgenic corn seed further comprises DNA encoding a protein active in the biosynthesis of lysine operably linked to the endosperm specific promoter. Aspects of the invention are corn cells having recombinant DNA comprising the DNA that is between the T-DNA borders of pMON99142 or the DNA that is between the T-DNA borders of pMON99143.

Another aspect of the invention provides recombinant DNA constructs that are effective in providing transgenic corn seed with enhanced levels of free lysine. Such a recombinant DNA construct comprises an embryo specific promoter operably linked to DNA for suppressing production of the endogenous LKR-SDH protein and an endosperm specific promoter operably linked to DNA for suppressing production of the endogenous LKR-SDH protein. An embodiment of the recombinant DNA further comprises DNA encoding a protein active in the biosynthesis of lysine operably linked to the endosperm specific promoter. Aspects of the recombinant DNA are illustrated by the DNA that is between the T-DNA borders of pMON99142 or pMON99143.

This invention also provides methods of producing corn kernels with enhanced levels of free lysine by propagating corn plants having transgenic cells which are progeny of a corn cell that has been transformed with a recombinant DNA construct of the invention.

DETAILED DESCRIPTION OF THE INVENTION

As used herein LKR-SDH means the lysine catabolic protein lysine ketoglutarate reductase/saccharopine dehydrogenase. Effective gene suppression elements for use in this invention are designed for either the LKR domain or the SDH domain.

Recombinant DNA constructs can be readily prepared by those skilled in the art using commercially available materials and well-known, published methods. Recombinant DNA constructs for gene suppression can be fabricated as illustrated and disclosed in US 2004-0029283 A1. A useful technology for building recombinant DNA constructs and vectors for transformation is the GATEWAY™ cloning technology (available from Invitrogen Life Technologies, Carlsbad, Calif.) uses the site specific recombinase LR cloning reaction of the Integrase att system from bacteriophage lambda vector construction, instead of restriction endonucleases and ligases. The LR cloning reaction is disclosed in U.S. Pat. Nos. 5,888,732 and 6,277,608 and US Patent Application Publications US 2001-283529 A1, US 2001-282319 A1, US 2002-0007051 A1, and US 2004-0115642 A1. The GATEWAY™ Cloning Technology Instruction Manual which is also supplied by Invitrogen also provides concise directions for routine cloning of any desired DNA into a vector comprising operable plant expression elements.

An alternative vector fabrication method employs ligation-independent cloning as disclosed by Aslandis, C. et al., Nucleic Acids Res., 18, 6069-6074, 1990 and Rashtchian, A. et al., Biochem., 206, 91-97, 1992 where a DNA fragment with single-stranded 5' and 3' ends are ligated into a desired vector which can then be amplified in vivo. Methods for assembling DNA molecules in a predetermined order in a DNA construct are also disclosed in published patent application US 2006-0147061 (Ser. No. 11/298,234).

Numerous promoters that are active in plant cells have been described in the literature. Useful promoters for the transgenic seed of this invention include promoters from seed genes such as napin (U.S. Pat. No. 5,420,034), cornL3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), peroxiredoxin antioxidant (Per1) (Stacy et al. (1996) *Plant Mol. Biol.* 31(6):1205-1216), and B32 (Hartings et al. (1990) *Plant Mol. Biol.*, 14:1031-1040)

In practice DNA is introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable markers are illustrated in U.S. Pat. Nos. 5,550,318; 5,633,435; 5,780,708 and 6,118,047. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

The invention provides transgenic seed having in its genome a recombinant DNA construct comprising (a) a plant endosperm-specific promoter operably linked to at least one first gene suppression element for suppressing the production of a lysine catabolic protein, e.g. LKR-SDH, and (b) a plant embryo-specific promoter in the opposite orientation to the plant endosperm-specific promoter and located 3' to the at least one first gene suppression element. The plant embryo-specific promoter is operably linked to a second gene suppression element for suppressing the production of the lysine catabolic protein LKR-SDH. The second gene suppression element can comprise same DNA as the first gene suppression element or different DNA, e.g. targeted to a different domain of the LKR-SDH gene. The gene suppression element can be assembled in a recombinant DNA construct in the same orientation or in opposing orientations, e.g. with adjacent promoters (head-to-head) or with adjacent terminators (tail-to-tail).

In some embodiments of the transgenic seed, the recombinant DNA construct further includes DNA encoding a lysine biosynthesis enzyme linked to the endosperm-specific promoter. In embodiments where both a gene suppression element and an expression element for expressing a protein are operably linked to one promoter, the gene suppression element can be embedded in an intron, which in many embodiments is preferably a transcription-enhancing intron, e.g., "enhancers" such as 5' introns from the rice actin 1 gene, rice actin 2 gene, the corn alcohol dehydrogenase gene, the corn heat shock protein 70 gene, and the corn shrunken 1 gene. Useful DNA for encoding a lysine biosynthesis enzyme is from an exogenous lysine-insensitive dihydrodipicolinic acid synthase (DHDPS) gene such as the Corynebacterium DHDPS gene as disclosed in U.S. Pat. Nos. 5,773,691 and 6,459,019. When expressing DNA encoding a DHDPS enzyme, it is useful to have it linked to DNA encoding a transit peptide such as from a maize DHDPS transit peptide gene.

The invention provides transgenic plant cells having a recombinant DNA construct of this invention stably integrated into their genome such that the recombinant DNA is inherited by progeny plants and seeds. Certain embodiments of such transgenic plant cells are homozygous for the recombinant DNA.

This invention further provides recombinant DNA constructs for transformation of plant cells, methods for their use, and stably transgenic plant cells containing such constructs. Such recombinant DNA constructs are found on plasmids pMON99142 and pMON99143, described in more detail below.

Numerous methods for transforming plant cells with recombinant DNA are known in the art and may be used to prepare transgenic maize. Two commonly used methods for plant transformation are Agrobacterium-mediated transformation and microprojectile bombardment. Microprojectile bombardment methods for producing transgenic corn cells are illustrated in U.S. Pat. Nos. 5,550,318; 5,538,880; 6,160,208 and 6,399,861 and Agrobacterium-mediated transformation for producing transgenic corn cells is described in U.S. Pat. No. 5,591,616. For Agrobacterium tumefaciens based plant transformation systems, additional elements present on transformation constructs include T-DNA left and/or right border sequences from Agrobacterium tumefaciens (generally both left and right border sequences, but preferably at least one border sequence, e.g. at least a right border sequence) to facilitate incorporation of the recombinant polynucleotide into the plant genome.

Transformation of corn is preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. Nos. 6,194,636 and 6,232,526 and U.S. patent application publication US 2004-0216189 A1.

The seeds of transgenic plants can be harvested from fertile transgenic plants and be used to grow progeny generations of transformed plants of this invention including hybrid plant lines comprising the recombinant DNA construct expressing the genes suppression elements.

This invention further provides various methods for producing transgenic corn seed having an enhance level of lysine, i.e. at least 1300 ppm free lysine or more, e.g. at least 1500 ppm or higher, say, at least 2000 ppm or 300 ppm, up to 4000 ppm of free lysine. Such methods comprise transformation of a corn plant line and introgressing the recombinant DNA of this invention from a corn plant having the recombinant DNA in its cells into another corn plant line. One aspect of such methods comprises (a) selecting a first transgenic corn plant comprising in its cells a recombinant DNA construct of this invention; (b) introgressing the recombinant DNA construct into a second corn plant; (c) growing seed from the second corn plant to produce a population of progeny corn plants; (d) screening the population of progeny corn plants for progeny corn plants that produce corn seed having an increased level of lysine relative to non-transgenic corn plants; (e) selecting from the population one or more progeny corn plants that produce corn seed having an enhanced level of lysine relative to non-transgenic corn plants; (f) verifying that the recombinant DNA construct is stably integrated in the selected progeny corn plants; (g) verifying that the LKR-SDH lysine catabolism gene is silenced in the selected progeny corn plants relative to corn plants lacking the recombinant DNA construct; (h) collecting transgenic corn seed from the selected progeny corn plants.

Example 1

Figure 1:
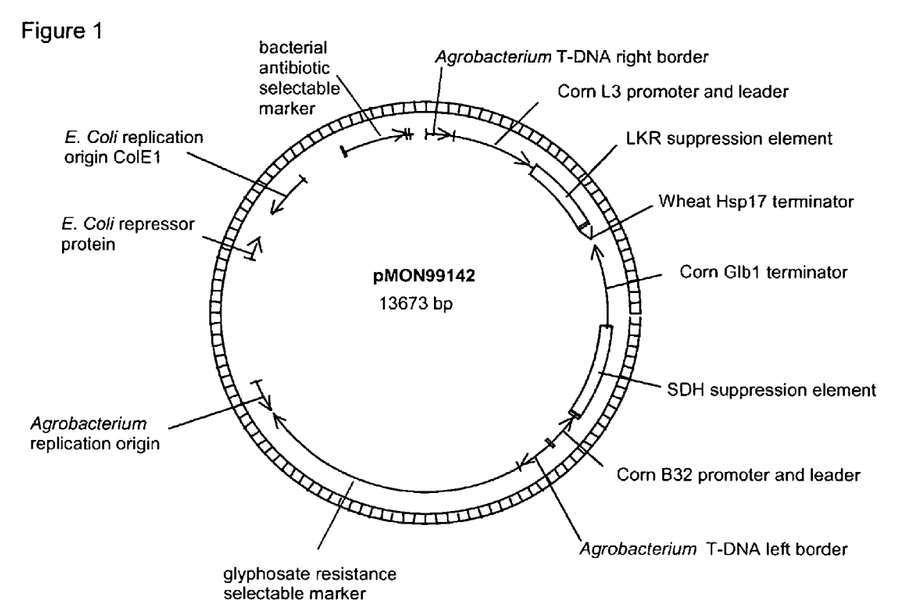
FIGS. 1 and 2 illustrate plasmid maps.

This example illustrates the preparation of a recombinant DNA construct useful for preparing the transgenic corn plants and seed with transgenic cells of this invention. With reference to FIG. 1 and SEQ ID NO: 1 (which is the nucleotide sequence of one strands of the DNA in the plasmid pMON99142) a plant transformation plasmid was prepared with two gene suppression recombinant DNA constructs inserted between left and right T-DNA borders from *Agrobacterium tumefaciens*. Between the T-DNA borders were (a) an LKR gene suppression recombinant DNA construct which was prepared with DNA for a cornL3 promoter and leader (i.e. a corn embryo specific promoter and leader from cornL3 oleosin gene as disclosed in U.S. Pat. No. 6,433,252), operably linked to DNA for an "LKR suppression element" (a stabilized anti-sense construct comprising about 947 base pairs of DNA from the LKR domain of a corn LKR-SDH gene arranged as an anti-sense oriented segment) followed by sense oriented segment and terminated with DNA for a wheat hsp17 terminator (i.e. polyadenylation site and signal from a *Triticum aestivum* heat shock protein 17 gene); and (b) an SDH gene suppression recombinant DNA construct which was prepared with DNA for a corn B32 promoter and leader (i.e. a corn endosperm specific promoter and leader from corn B32 gene disclosed as nucleotides 848 through 1259 of GenBank accession number X70153), operably linked to DNA for an "SDH suppression element" (a stabilized anti-sense construct comprising about 1254 base pairs of DNA from the SDH domain of a corn LKR-SDH gene arranged as an anti-sense oriented segment followed by sense oriented segment) and terminated with DNA for a corn Glb1 terminator (i.e. polyadenylation site and signal from a *Zea mays* globulin 1 gene).

The plasmid also contained outside of the T-DNA borders DNA for a glyphosate resistance selectable marker, an *Agrobacterium* replication origin, an *E. coli* repressor protein, an *E. coli* replication origin ColE1, and a bactericidal antibiotic selectable marker (for spectromycin/streptomycin). The DNA for the glyphosate resistance marker comprised a rice actin 1 promoter, leader and intron operably linked to chimeric DNA encoding a chloroplast transit peptide and an EPSPS gene and DNA from a terminator element with a polyadenylation site and signal from *A. tumefaciens* nopoline synthase. Table 1 shows the position of key elements of the plasmid with respect to SEQ ID NO:1. The SDH gene suppression recombinant DNA construct and the LKR gene suppression recombinant DNA constructs were arranged tail-to-tail. Thus, in the following Table 1 the DNA in SEQ ID NO:1 identified for the elements of the LKR gene suppression recombinant DNA construct comprises nucleotides in the reverse complement of the coding strand for those elements. The plasmid pMON99142 is deposited with the ATCC on May 12, 2006 under ATCC Accession No. PTA-7595.

TABLE 1

| Element | Coordinates on pMON99142 SEQ ID NO: 1 |
|---|---|
| *Agrobacterium* T-DNA right border | 1-331 |
| Corn L3 promoter and leader | 345-1383 |
| LKR suppression element | 1396-2343 |
| Wheat Hsp17 terminator | 2349-2558 |
| Corn Glb1 terminator | 2589-3582 |
| SDH suppression element | 3588-4742 |
| Corn B32 promoter and leader | 4747-5179 |
| *Agrobacterium* T-DNA left border | 5235-5676 |
| glyphosate resistance selectable marker | 5683-8954 |

TABLE 1-continued

| Element | Coordinates on pMON99142 SEQ ID NO: 1 |
|---|---|
| *Agrobacterium* replication origin | 9006-9402 |
| *E. coli* ColE1 repressor protein | 10911-11102 |
| *E. coli* replication origin, ColE1 | 11530-12118 |
| bacterial antibiotic selectable marker | 12649-13537 |

Example 2

This example illustrates the preparation of a recombinant DNA construct useful for preparing the transgenic corn plants and seed with transgenic cells of this invention. With reference to Example 1 and FIGS. 2 and 3 and SEQ ID NO:2 (which is the nucleotide sequence of one strands of the DNA in the plasmid pMON99143) a plant transformation plasmid was prepared with two gene suppression recombinant DNA constructs inserted between left and right T-DNA borders from *Agrobacterium tumefaciens*. Between the T-DNA borders were (a) an SDH gene suppression recombinant DNA construct which was prepared with a corn B32 endosperm specific promoter and leader operably linked in series to a corn Hsp70 intron (i.e. from a *Zea mays* heat shock protein 70 gene) into which embedded an "SDH suppression element", where the intron was linked to DNA encoding a corn DHDPS transit peptide (i.e. from a *Zea mays* dihydrodipicolinic acid transit peptide gene) linked to DNA encoding *Corynebacterium* DHDPS (i.e. from a lysine-insensitive *Corynebacterium* DHDPS gene) and terminated with DNA for a wheat HSP17 terminator; and (b) an LKR gene suppression recombinant DNA construct which was prepared with a corn L3 embryo specific promoter and leader operably linked in series to an "LKR suppression element" and terminated with DNA for a corn Glb1 terminator.

Figure 2:
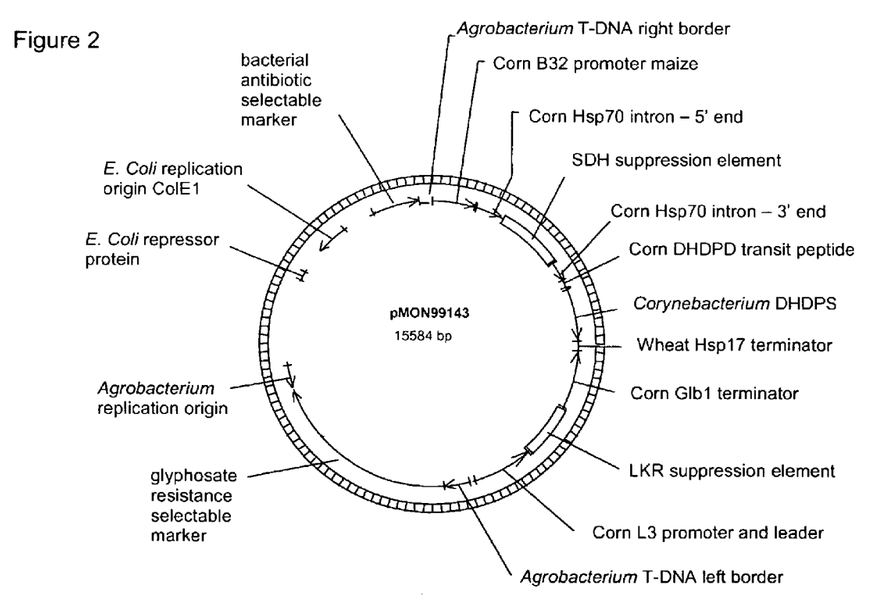
Figure 3:
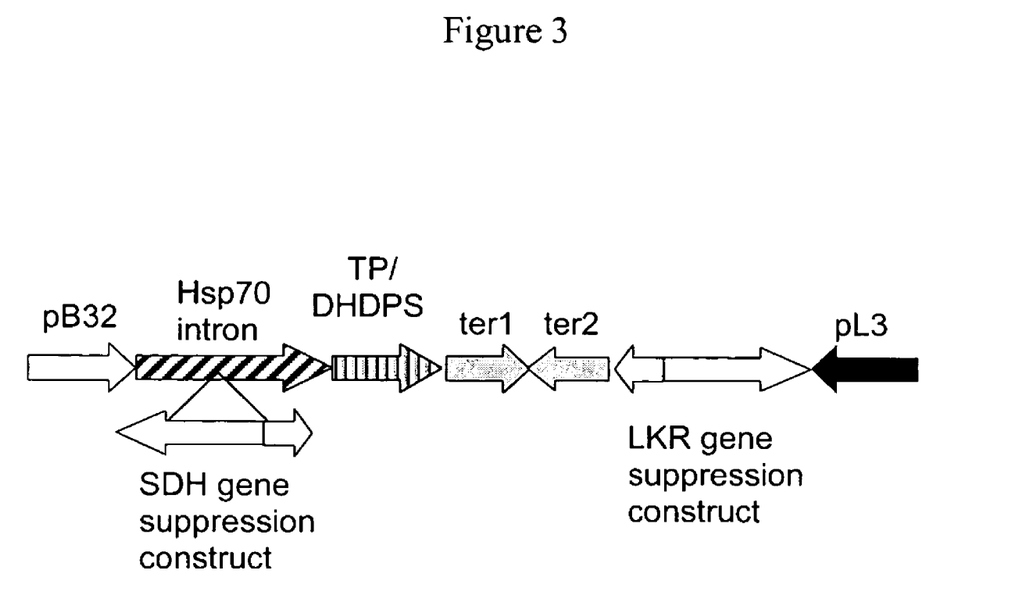
FIG. 3 schematically illustrates a recombinant DNA construct.

The plasmid also contained outside of the T-DNA borders DNA for a glyphosate resistance selectable marker, an *Agrobacterium* replication origin, an *E. coli* repressor protein, an *E. coli* replication origin ColE1, and a bactericidal antibiotic selectable marker (for spectromycin/streptomycin). Table 2 shows the position of elements of the plasmid with respect to SEQ ID NO:2. The SDH gene suppression recombinant DNA construct and the LKR gene suppression recombinant DNA constructs were arranged tail-to-tail. Thus, in the following Table 2 the DNA in SEQ ID NO:2 identified for the elements of the LKR gene suppression recombinant DNA construct comprises nucleotides in the reverse complement of the coding strand for those elements. The plasmid pMON99143 is deposited with the ATCC on May 12, 2006 under ATCC Accession No. PTA-7596.

TABLE 2

| Element | Coordinates on pMON99143 SEQ ID NO: 2 |
|---|---|
| *Agrobacterium* T-DNA right border | 1-357 |
| corn B32 endosperm specific promoter and leader | 374-806 |
| Corn Hsp70 intron - 5' end | 812-1256 |
| SDH suppression element | 1270-2424 |
| Corn Hsp70 intron - 3' end | 2429-2778 |
| Corn DHDPS transit peptide | 2783-2953 |
| *Corynebacterium* DHDPS | 2954-3856 |
| Wheat Hsp17 terminator | 3862-4071 |
| Corn Glb1 terminator | 4091-5084 |

TABLE 2-continued

| Element | Coordinates on pMON99143 SEQ ID NO: 2 |
|---|---|
| LKR suppression element | 5091-6038 |
| Corn L3 promoter and leader | 6051-7089 |
| *Agrobacterium* T-DNA left border | 7146-7587 |
| Glyphosate resistance selectable marker | 7594-10865 |
| *Agrobacterium* replication origin | 10917-11313 |
| *E. coli* ColE1 repressor protein | 12822-13013 |
| *E. coli* replication origin, ColE1 | 13441-14029 |
| Bacterial antibiotic selection | 14560-15448 |

Example 3

This example illustrates the use of the plasmid of Example 1 for producing transgenic corn cells and plants and seed of fertile transgenic corn with enhanced levels of free lysine. Plasmid pMON99142 is inserted into corn callus by *Agrobacterium*-mediated transformation to produce multiple transgenic events of corn cells that are selected as being resistant to glyphosate herbicide (based on insertion of the DNA for the glyphosate resistance selectable marker from one side of the T-DNA borders). Transgenic plants (R0) are grown from transformed cells of each of the multiple transgenic events. The R0 transgenic corn plants are analyzed for the presence of the glyphosate resistance marker DNA and the gene suppression recombinant DNA constructs using fluorescent-tagged probes that hybridize to PCR-amplified segments of the plasmids. From the multiple plants representing the transgenic events plants are selected which have the glyphosate resistance selectable marker DNA at a single locus and a single copy of the T-DNA comprising the SDH and LKR gene suppression recombinant DNA constructs at a separate single locus. The single copy-single locus T-DNA plants are crossed with a non-transgenic inbred corn line to produce segregating progeny seed which is analyzed to identify seeds with gene suppression recombinant DNA and without DNA for the glyphosate resistant selectable marker. Seed analysis is effected on DNA from a chip of endosperm. The identified seeds are grown into plants that are crossed with several inbred corn lines over several generations to introgress the T-DNA comprising the SDH and LKR gene suppression recombinant DNA constructs into the inbred corn lines to produce inbred corn lines with DNA for suppressing the lysine catabolic protein LKR/SDH in both the endosperm and embryo.

Seeds from transgenic corn plants of the inbred corn lines with DNA for suppressing the lysine catabolic protein LKR/SDH in both the endosperm and embryo are analyzed for free lysine and determined to have greater than 1300 ppm lysine. Seeds from inbred corn line plants having cells with selected transgenic events are identified as having greater than 1500 ppm free lysine, greater than 2000 ppm free lysine, greater than 3000 ppm free lysine and greater than 4000 ppm free lysine.

Example 4

This example illustrates the use of the plasmid of Example 2 for producing transgenic corn cells and plants and seed of fertile transgenic corn with enhanced levels of free lysine. The transformation, analysis, selecting and introgressing of Example 3 are essentially reproduced using plasmid pMON99143 to provide inbred corn lines with DNA for suppressing the lysine catabolic protein LKR/SDH in both the endosperm and embryo as well as expressing the *Corynebacterium* DHDPS enzyme. Seeds from inbred corn line plants having cells with selected transgenic events are identified as having greater than 1500 ppm free lysine, greater than 2000 ppm free lysine, greater than 3000 ppm free lysine and greater than 4000 ppm free lysine.

What is claimed is:

1. A transgenic corn seed having at least 1300 ppm free lysine and having in its genome a recombinant DNA construct comprising: (a) an embryo specific promoter operably linked to at least one first gene suppression element for suppressing production of the endogenous LKR-SDH protein and (b) an endosperm specific promoter operably linked to a second gene suppression element for suppressing production of the endogenous LKRSDH protein, wherein said endosperm specific promoter is in the opposite orientation to the plant endosperm-specific promoter, wherein said recombinant DNA comprises all of the DNA that is between the T-DNA borders of pMON99142 or pMON99143 and that includes said embryo specific promoter and said endosperm specific promoter.

2. A transgenic corn seed of claim 1 further comprising DNA encoding a protein active in the biosynthesis of lysine operably linked to said endosperm specific promoter.

3. A transgenic corn seed of claim 2 wherein said recombinant DNA comprises all of the DNA that is between the T-DNA borders of pMON99143 and that includes said embryo specific promoter and said endosperm specific promoter.

4. A recombinant DNA construct that is effective in providing transgenic corn seed having at least 1300 ppm free lysine, wherein said recombinant DNA construct comprises an embryo specific promoter operably linked to DNA for suppressing production of the endogenous LKR-SDH protein and an endosperm specific promoter operably linked to DNA for suppressing production of the endogenous LKR-SDH protein, wherein said endosperm specific promoter is in the opposite orientation to the plant endosperm-specific promoter, wherein said recombinant DNA comprises all of the DNA that is between the T-DNA borders of pMON99142 or pMON99143 and that includes said embryo specific promoter and said endosperm specific promoter.

5. The recombinant DNA construct of claim 4 further comprising DNA encoding a protein active in the biosynthesis of lysine operably linked to said endosperm specific promoter.

6. The recombinant DNA construct of claim 5 wherein said recombinant DNA comprises all of the DNA that is between the T-DNA borders of pMON99143 and that includes said embryo specific promoter and said endosperm specific promoter.

* * * * *

SEQUENCE LISTING

```
<160> NUMBER OF SEQ ID NOS: 2

<210> SEQ ID NO 1
<211> LENGTH: 13673
<212> TYPE: DNA
<213> ORGANISM: Artificial Sequence
<220> FEATURE:
<221> NAME/KEY: misc_feature
<222> LOCATION: (1)..(13673)
<223> OTHER INFORMATION: Synthetic Plasmid DNA Molecule

<400> SEQUENCE: 1 aggattttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc cgattattct aataaacgct cttttctctt aggtttaccc     300
gccaatatat cctgtcaaac actgatagtt tatccgtcga ggtcactaag caactaactt     360
tgaggaatga ggtgatgatg aattaactca ctccattcca caaaccaaac aaaaatttga     420
ggagtgagaa gatgattgac tatctcattc ctcaaaccaa acacctcaaa tatatctgct     480
atcgggattg gcattcctgt atccctacgc ccgtgtaccc cctgtttaga gaacctccaa     540
```

-continued

| | |
|---|---|
| aggtataaga tggcgaagat tattgttgtc ttgtctttca tcatatatcg agtctttccc | 600 |
| taggatatta ttattggcaa tgagcattac acggttaatc gattgagaga acatgcatct | 660 |
| caccttcagc aaataattac gataatccat attttacgct tcgtaacttc tcatgagttt | 720 |
| cgatatacaa atttgttttc tggacaccct accattcatc ctcttcggag aagagaggaa | 780 |
| gtgtcctcaa tttaaatatg ttgtcatgct gtagttcttc acaaaatctc aacaggtacc | 840 |
| aagcacattg tttccacaaa ttatatttta gtcacaataa atctatatta ttattaatat | 900 |
| actaaaacta tactgacgct cagatgcttt tactagttct tgctagtatg tgatgtaggt | 960 |
| ctacgtggac cagaaaatag tgagacacgg aagacaaaag aagtaaaaga ggcccggact | 1020 |
| acggcccaca tgagattcgg ccccgccacc tccggcaacc agcggccgat ccaacggcag | 1080 |
| tgcgcgcaca cacacaacct cgtatatatc gccgcgcgga agcggcgcga ccgaggaagc | 1140 |
| cttgtcctcg acacccccta cacaggtgtc gcgctgcccc cgacacgagt cccgcatgcg | 1200 |
| tcccacgcgg ccgcgccaga tcccgcctcc gcgcgttgcc acgccctcta taaacaccca | 1260 |
| gctctcccctc gccctcatct acctcactcg tagtcgtagc tcaagcatca gcggcagcgg | 1320 |
| cagcggcagg atctctgggc agcgtgcgca cgtggggtat ctagctcgct ctgctagcct | 1380 |
| accagatcct gcggatctta aaggatcat accgaaagaa aggcctctct attgatgtac | 1440 |
| tcttgttgat aaattcaatg gaacctccaa tatcacaagt tatgtcacaa acgccgacta | 1500 |
| aaggacaacc agtctccatc aattgctgta actgatccat atttagtaat ggtggaaacc | 1560 |
| tcttctccca atacatacag tttacgatga cagatgcata tggagcaatt ctttcatgaa | 1620 |
| aaacaggggt gtagtgttct ggatgagcat aatagtcacc tttgtcaaat tgtctggtgg | 1680 |
| gatccttgtg agaaaccatg tctctagagg tcacaacaca accataaagt tgaaatactc | 1740 |
| tcttggtcga ctgagattgc ttagacagat tcctggcctg aaaaatttcg ggaagcttct | 1800 |
| cagcatcaac aaaggtatgg ggcaataact tgaatatctc ctgcgcaccc tgagagacgt | 1860 |
| ttccaactcc agtgaacaca aacactatcg gacaaattcc ggatggaagt ccaaatgttg | 1920 |
| ctatctcttc tgcaacgaca atgactgcag cctaccggtt tcaggccagg aatctgtcta | 1980 |
| agcaatctca gtcgaccaag agagtatttc aactttatgg ttgtgttgtg acctctagag | 2040 |
| acatggtttc tcacaaggat cccaccagac aatttgacaa aggtgactat tatgctcatc | 2100 |
| cagaacacta caccccctgtt tttcatgaaa gaattgctcc atatgcatct gtcatcgtaa | 2160 |
| actgtatgta ttgggagaag aggtttccac cattactaaa tatggatcag ttacagcaat | 2220 |
| tgatggagac tggttgtcct ttagtcggcg tttgtgacat aacttgtgat attggaggtt | 2280 |
| ccattgaatt tatcaacaag agtacatcaa tagagaggcc tttctttcgg tatgatcctt | 2340 |
| ctagaattct gcatgcgttt ggacgtatgc tcattcaggt tggagccaat ttggttgatg | 2400 |
| tgtgtgcgag ttcttgcgag tctgatgaga catctctgta ttgtgttttct ttccccagtg | 2460 |
| ttttctgtac ttgtgtaatc ggctaatcgc caacagattc ggcgatgaat aaatgagaaa | 2520 |
| taaattgttc tgattttgag tgcaaaaaaa aaggaattga tatcggcgcg cctcgagtgg | 2580 |
| cggccgcgtt ttatgaataa taataatgca tatctgtgca ttactacctg ggatacaagg | 2640 |
| gcttctccgc cataacaaat tgagttcgca tgctgagaac gaacggggaa gaaagtaagc | 2700 |
| gccgcccaaa aaaacgaac atgtacgtcg gctatagcag gtgaaagttc gtgcgccaat | 2760 |
| gaaaagggaa cgtatatgcgt tgggtagttg ggatacttaa attggagag tttgttgcat | 2820 |
| acactaatcc actaaagttg tctatctttt taacagctct aggcaggata taagatttat | 2880 |
| atctaatctg ttggagttgc ttttagagta acttttctct ctgtttcgtt tatagccgat | 2940 |

```
tagcacaaaa ttaaactagg tgacgagaaa taaagaaaaa cggaggcagt aaaaaatacc    3000 caaaaaata cttggagatt tttgtctcaa aattatcttc taattttaaa agctacatat     3060
taaaaatact atatattaaa aatacttcga gatcattgct tgggatgggc agggccaata    3120
gctaattgct aaggatgggc tatatttatg tatcgtctga acatgtagg ggctaatagt     3180 tagatgacta atttgctgtg ttcgtacggg gtgctgtttg agcctagcga tgaagggtca    3240
tagtttcata caagaactca cttttggttc gtctgctgtg tctgttctca gcgtaacggc    3300
atcaatggat gccaaactcc gcaaggggac aaatgaagaa gcgaagagat tatagaacac    3360
gcacgtgtca ttatttattt atggacttgc ctcagtagct tacagcatcg tacccgcacg    3420
tacatactac agagccacac ttattgcact gcctgccgct tacgtacata gttaacacgc    3480
agagaggtat atacatacac gtccaacgtc tccactcagg ctcatgctac gtacgcacgt    3540
cggtcgcgcg ccaccctctc gttgcttcct gctcgttttg gcgaattccg atttggcaag    3600
tgttccagag caaagctgg aagctctcgt agtctgagcc tctttgctga ttcatacaag     3660
ttatgaccat ctacatggat cgtctcacca agaaatttgt agactgcagg attttttccct   3720 gaccggagtg caccagctgg gttccaactg aatttatagg caagcggatt gtttgctgca    3780
gctggagatg gcaatccacc acagtaagat gtaaatgcct ttatttttcc ctttcgtgca    3840
tgagcttcat caatcatctt cattgacatc aagtgatcta tgccaggatc taggcccatt    3900
tcacaaagta tagttacacc tgcatctttg gcagcttggc tcaagtttga catggattca    3960
tcaacatagc ttgccgttac catgtgcttc ttcaactcta tgcatactcc tgcaatggca    4020
gcatgaaaac tagcaggcag caccggtttg gagctggaag agtctgtcgg ccagctgctg    4080
agtttctggc atcttaccca gacatatgta cctatggtgt tgatgaccat gatgcagatc    4140
aaattcatgt tatcgtggca tctttgtatc aaaaagatgc agaagagaca gttgatggta    4200
ttgaaaatac aactgctacc cagcttgatg ttgctgatat tggaagcctt tcagatcttg    4260
tttctcaggt tgaggttgta attagcttgc tgcctgctag ttttcatgct gccattgcag    4320
gagtatgcat agagttgaag aagcacatgg taacggcaag ctatgttgat gaatccatgt    4380
caaacttgag ccaagctgcc aaagatgcag gtgtaactat actttgtgaa atgggcctag    4440
atcctggcat agatcacttg atgtcaatga agatgattga tgaagctcat gcacgaaagg    4500
gaaaaataaa ggcatttaca tcttactgtg gtggattgcc atctccagct gcagcaaaca    4560
atccgcttgc ctataaattc agttggaacc cagctggtgc actccggtca gggaaaaatc    4620
ctgcagtcta caaatttctt ggtgagacga tccatgtaga tggtcataac ttgtatgaat    4680
cagcaaagag gctcagacta cgagagcttc cagcttttgc tctggaacac ttgccaaatc    4740
gggatctccc ttcgagctct tttgtatcaa cagctaaaat gatggatggg tttttgtaag    4800
cattgtgaat tgggatgatg tgctaccaga gatatatata gtgggagagc ttggggcat     4860 gcagccatgt tggtagtcta tatctatgta tctatattag ccatgtcatc atactaactt    4920
ccaacctttc gatgaaagca aaaactatcc atatcatctc ccactaactt tccacatcat    4980
ctcgtcctac taatagtcat gtcatcccac taacatccaa cctcttaatg aaatctattc    5040
acgtcaactt ttttttatag gacaggaggg gcaagcccct actgaaattt tattaaaatt    5100
ttaaaacgac agagttagaa gcatacagga aagtaaatta taaattacaa aattacaaaa    5160
gggaaaaatt gacgagatca agcttactag cccgggcgcg ccttaattaa gcggccgcat    5220
cgatcgtgaa gtttctcatc taagccccca tttggacgtg aatgtagaca cgtcgaaata    5280
aagatttccg aattagaata atttgtttat tgctttcgcc tataaatacg acggatcgta    5340
```

```
atttgtcgtt ttatcaaaat gtactttcat tttataataa cgctgcggac atctacattt    5400
ttgaattgaa aaaaaattgg taattactct ttcttttttct ccatattgac catcatactc   5460
attgctgatc catgtagatt tcccggacat gaagccattt acaattgaat atatcctgcc    5520
gccgctgccg ctttgcaccc ggtggagctt gcatgttggt ttctacgcag aactgagccg    5580
gttaggcaga taatttccat tgagaactga gccatgtgca ccttcccccc aacacggtga    5640
gcgacggggc aacggagtga tccacatggg acttttgtac actcgaggtc attcatatgc    5700
ttgagaagag agtcgggata gtccaaaata aaacaaaggt aagattacct ggtcaaaagt    5760
gaaaacatca gttaaaaggt ggtataaagt aaaatatcgg taataaaagg tggcccaaag    5820
tgaaatttac tcttttctac tattataaaa attgaggatg ttttttgtcgg tactttgata   5880 cgtcattttt gtatgaattg gttttttaagt ttattcgctt ttggaaatgc atatctgtat    5940
ttgagtcggg ttttaagttc gtttgctttt gtaaatacag agggatttgt ataagaaata    6000
tctttagaaa aacccatatg ctaatttgac ataattttg agaaaaatat atattcaggc     6060
gaattctcac aatgaacaat aataagatta aaatagcttt cccccgttgc agcgcatggg    6120 tatttttttct agtaaaaata aaagataaac ttagactcaa acatttaca aaaacaaccc    6180 ctaaagttcc taaagcccaa agtgctatcc acgatccata gcaagcccag cccaacccaa    6240
cccaacccaa cccaccccag tccagccaac tggacaatag tctccacacc cccccactat    6300
caccgtgagt tgtccgcacg caccgcacgt ctcgcagcca aaaaaaaaaa gaaagaaaaa    6360
aaagaaaaag aaaaaacagc aggtgggtcc gggtcgtggg ggccggaaac gcgaggagga    6420
tcgcgagcca gcgacgaggc cggccctccc tccgcttcca agaaacgcc ccccatcgcc     6480 actatataca tacccccccc tctcctccca tccccccaac cctaccacca ccaccaccac    6540
cacctccacc tcctcccccc tcgctgccgg acgacgagct cctcccccct cccctccgc     6600 cgccgccgcg ccggtaacca ccccgcccct ctcctctttc tttctccgtt ttttttttccg   6660 tctcggtctc gatctttggc cttggtagtt tgggtgggcg agaggcggct tcgtgcgcgc    6720
ccagatcggt gcgcgggagg ggcgggatct cgcggctggg gctctcgccg gcgtggatcc    6780
ggcccggatc tcgcggggaa tggggctctc ggatgtagat ctgcgatccg ccgttgttgg    6840
gggagatgat gggggttta aaatttccgc cgtgctaaac aagatcagga agagggaaa     6900 agggcactat ggtttatatt tttatatatt tctgctgctt cgtcaggctt agatgtgcta    6960
gatctttctt tcttcttttt gtgggtagaa tttgaatccc tcagcattgt tcatcggtag    7020 ttttctttt catgatttgt gacaaatgca gcctcgtgcg gagcttttttt gtaggtagaa    7080 gtgatcaacc atggcgcaag ttagcagaat ctgcaatggt gtgcagaacc catctcttat    7140
ctccaatctc tcgaaatcca gtcaacgcaa atctcccctta tcggtttctc tgaagacgca   7200
gcagcatcca cgagcttatc cgatttcgtc gtcgtgggga ttgaagaaga gtgggatgac    7260
gttaattggc tctgagcttc gtcctcttaa ggtcatgtct tctgtttcca cggcgtgcat    7320
gcttcacggt gcaagcagcc ggcccgcaac cgcccgcaaa tcctctggcc tttccggaac    7380
cgtccgcatt cccggcgaca agtcgatctc ccaccggtcc ttcatgttcg gcggtctcgc    7440
gagcggtgaa acgcgcatca ccggccttct ggaaggcgag gacgtcatca atacgggcaa    7500
ggccatgcag gcgatgggcg cccgcatccg taaggaaggc gacacctgga tcatcgatgg    7560
cgtcggcaat ggcggcctcc tggcgcctga ggcgccgctc gatttcggca atgccgccac    7620
gggctgccgc ctgacgatgg gcctcgtcgg ggtctacgat ttcgcagca ccttcatcgg     7680 cgacgcctcg ctcacaaagc gcccgatggg ccgcgtgttg aacccgctgc gcgaaatggg    7740
```

-continued

```
cgtgcaggtg aaatcggaag acggtgaccg tcttcccgtt accttgcgcg ggccgaagac   7800
gccgacgccg atcacctacc gcgtgccgat ggcctccgca caggtgaagt ccgccgtgct   7860
gctcgccggc ctcaacacgc ccggcatcac gacggtcatc gagccgatca tgacgcgcga   7920
tcatacggaa aagatgctgc agggcttttgg cgccaacctt accgtcgaga cggatgcgga   7980
cggcgtgcgc accatccgcc tggaaggccg cggcaagctc accggccaag tcatcgacgt   8040
gccgggcgac ccgtcctcga cggccttccc gctggttgcg gccctgcttg ttccgggctc   8100
cgacgtcacc atcctcaacg tgctgatgaa ccccacccgc accggcctca tcctgacgct   8160
gcaggaaatg ggcgccgaca tcgaagtcat caacccgcgc cttgccggcg gcgaagacgt   8220
ggcggacctg cgcgttcgct cctccacgct gaagggcgtc acggtgccgg aagaccgcgc   8280
gccttcgatg atcgacgaat atccgattct cgctgtcgcc gccgccttcg cggaagggcc   8340
gaccgtgatg aacggtctgg aagaactccg cgtcaaggaa agcgaccgcc tctcggccgt   8400
cgccaatggc ctcaagctca atggcgtgga ttgcgatgag ggcgagacgt cgctcgtcgt   8460
gcgtggccgc cctgacggca aggggctcgg caacgcctcg ggcgccgccg tcgccaccca   8520
tctcgatcac cgcatcgcca tgagcttcct cgtcatgggc ctcgtgtcgg aaaaccctgt   8580
cacggtggac gatgccacga tgatcgccac gagcttcccg gagttcatgg acctgatggc   8640
cgggctgggc gcgaagatcg aactctccga tacgaaggct gcctgatgag ctcgaattcc   8700
cgatcgttca acatttggc aataaagttt cttaagattg aatcctgttg ccggtcttgc   8760
gatgattatc atataatttc tgttgaatta cgttaagcat gtaataatta acatgtaatg   8820
catgacgtta tttatgagat gggtttttat gattagagtc ccgcaattat acatttaata   8880
cgcgatagaa aacaaaatat agcgcgcaaa ctaggataaa ttatcgcgcg cggtgtcatc   8940
tatgttacta gatcggggat gggggatctc agcccctggg gggatgggag gcccgcgtta   9000
gcgggccggg agggttcgag aagggggggc accccccttc ggcgtgcgcg gtcacgcgca   9060
cagggcgcag ccctggttaa aaacaaggtt tataaatatt ggtttaaaag caggttaaaa   9120
gacaggttag cggtggccga aaacggggcg gaaaccccttg caaatgctgg attttctgcc   9180
tgtggacagc ccctcaaatg tcaataggtg cgcccctcat ctgtcagcac tctgcccctc   9240
aagtgtcaag gatcgcgccc ctcatctgtc agtagtcgcg cccctcaagt gtcaataccg   9300
cagggcactt atcccaggc ttgtccacat catctgtggg aaactcgcgt aaaatcaggc   9360
gttttcgccg atttgcgagg ctggccagct ccacgtcgcc ggccgaaatc gagcctgccc   9420
ctcatctgtc aacgccgcgc cgggtgagtc ggccctcaa gtgtcaacgt ccgcccctca   9480
tctgtcagtg agggccaagt tttccgcgag gtatccacaa cgccggcggc cggccgcggt   9540
gtctcgcaca cggcttcgac ggcgtttctg gcgcgtttgc agggccatag acggccgcca   9600
gcccagcggc gagggcaacc agcccggtga gcgtcggaaa gggtcgatcg accgatgccc   9660
ttgagagcct tcaacccagt cagctccttc cggtgggcgc ggggcatgac tatcgtcgcc   9720
gcacttatga ctgtcttctt tatcatgcaa ctcgtaggac aggtgccggc agcgctctgg   9780
gtcattttcg gcgaggaccg ctttcgctgg agcgcgacga tgatcggcct gtcgcttgcg   9840
gtattcggaa tcttgcacgc cctcgctcaa gccttcgtca ctggtcccgc caccaaacgt   9900
ttcggcgaga agcaggccat tatcgccggc atggcggccg acgcgctggg ctacgtcttg   9960
ctggcgttcg cgacgcgagg ctggatggcc ttccccatta tgattcttct cgcttccggc  10020
ggcatcggga tgcccgcgtt gcaggccatg ctgtccaggc aggtagatga cgaccatcag  10080
ggacagcttc aaggatcgct cgcggctctt accagcctaa cttcgatcat tggaccgctg  10140
```

-continued

```
atcgtcacgg cgatttatgc cgcctcggcg agcacatgga acgggttggc atggattgta    10200
ggcgccgccc tataccttgt ctgcctcccc gcgttgcgtc gcggtgcatg gagccgggcc    10260
acctcgacct gaatggaagc cggcggcacc tcgctaacgg attcaccact ccaagaattg    10320
gagccaatca attcttgcgg agaactgtga atgcgcaaac caaccettgg cagaacatat    10380
ccatcgcgtc cgccatctcc agcagccgca cgcggcgcat ctcgggcagc gttgggtcct    10440
ggccacgggt gcgcatgatc gtgctcctgt cgttgaggac ccggctaggc tggcggggtt    10500
gccttactgg ttagcagaat gaatcaccga tacgcgagcg aacgtgaagc gactgctgct    10560
gcaaaacgtc tgcgacctga gcaacaacat gaatggtctt cggtttccgt gtttcgtaaa    10620
gtctggaaac gcggaagtca gcgccctgca ccattatgtt ccggatctgc atcgcaggat    10680
gctgctggct accctgtgga acacctacat ctgtattaac gaagcgctgg cattgaccct    10740
gagtgatttt tctctggtcc cgccgcatcc ataccgccag ttgtttaccc tcacaacgtt    10800
ccagtaaccg ggcatgttca tcatcagtaa cccgtatcgt gagcatcctc tctcgtttca    10860
tcggtatcat taccccccatg aacagaaatc ccccttacac ggaggcatca gtgaccaaac    10920
aggaaaaaac cgcccttaac atgggccgct ttatcagaag ccagacatta acgcttctgg    10980
agaaactcaa cgagctggac gcggatgaac aggcagacat ctgtgaatcg cttcacgacc    11040
acgctgatga gctttaccgc agctgcctcg cgcgtttcgg tgatgacggt gaaaacctct    11100
gacacatgca gctcccggag acggtcacag cttgtctgta agcggatgcc gggagcagac    11160
aagcccgtca gggcgcgtca gcgggtgttg gcgggtgtcg gggcgcagcc atgacccagt    11220
cacgtagcga tagcggagtg tatactggct taactatgcg gcatcagagc agattgtact    11280
gagagtgcac catatgcggt gtgaaatacc gcacagatgc gtaaggagaa ataccgcat    11340
caggcgctct tccgcttcct cgctcactga ctcgctgcgc tcggtcgttc ggctgcggcg    11400
agcggtatca gctcactcaa aggcggtaat acggttatcc acagaatcag gggataacgc    11460
aggaaagaac atgtgagcaa aaggccagca aaaggccagg aaccgtaaaa aggccgcgtt    11520
gctggcgttt ttccataggc tccgcccccc tgacgagcat cacaaaaatc gacgctcaag    11580
tcagaggtgg cgaaacccga caggactata aagataccag gcgtttcccc ctggaagctc    11640
cctcgtgcgc tctcctgttc cgaccctgcc gcttaccgga tacctgtccg cctttctccc    11700
ttcgggaagc gtggcgcttt ctcatagctc acgctgtagg tatctcagtt cggtgtaggt    11760
cgttcgctcc aagctgggct gtgtgcacga accccccgtt cagcccgacc gctgcgcctt    11820
atccggtaac tatcgtcttg agtccaaccc ggtaagacac gacttatcgc cactggcagc    11880
agccactggt aacaggatta gcagagcgag gtatgtaggc ggtgctacag agttcttgaa    11940
gtggtggcct aactacggct acactagaag gacagtattt ggtatctgcg ctctgctgaa    12000
gccagttacc ttcggaaaaa gagttggtag ctcttgatcc ggcaaacaaa ccaccgctgg    12060
tagcggtggt ttttttgttt gcaagcagca gattacgcgc agaaaaaaag gatctcaaga    12120
agatcctttg atcttttcta cggggtctga cgctcagtgg aacgaaaact cacgttaagg    12180
gattttggtc atgagattat caaaaaggat cttcacctag atcctttaa attaaaaatg    12240
aagttttaaa tcaatctaaa gtatatatga gtaaacttgg tctgacagtt accaatgctt    12300
aatcagtgag gcacctatct cagcgatctg tctatttcgt tcatccatag ttgcctgact    12360
ccccgtcgtg tagataacta cgatacggga gggcttacca tctggcccca gtgctgcaat    12420
gataccgcga gacccacgct caccggctcc agatttatca gcaataaacc agccagccgg    12480
aagggccgag cgcagaagtg gtcctgcaac tttatccgcc tccatccagt ctattaattg    12540
```

```
ttgccgggaa gctagagtaa gtagttcgcc agttaatagt ttgcgcaacg ttgttgccat    12600
tgctgcaggt cgggagcaca ggatgacgcc taacaattca ttcaagccga caccgcttcg    12660
cggcgcggct taattcagga gttaaacatc atgagggaag cggtgatcgc cgaagtatcg    12720
actcaactat cagaggtagt tggcgtcatc gagcgccatc tcgaaccgac gttgctggcc    12780
gtacatttgt acggctccgc agtggatggc ggcctgaagc cacacagtga tattgatttg    12840
ctggttacgg tgaccgtaag gcttgatgaa acaacgcggc gagctttgat caacgacctt    12900
ttggaaactt cggcttcccc tggagagagc gagattctcc gcgctgtaga agtcaccatt    12960
gttgtgcacg acgacatcat tccgtggcgt tatccagcta agcgcgaact gcaatttgga    13020
gaatggcagc gcaatgacat tcttgcaggt atcttcgagc cagccacgat cgacattgat    13080
ctggctatct tgctgacaaa agcaagagaa catagcgttg ccttggtagg tccagcggcg    13140
gaggaactct ttgatccggt tcctgaacag gatctatttg aggcgctaaa tgaaacctta    13200
acgctatgga actcgccgcc cgactgggct ggcgatgagc gaaatgtagt gcttacgttg    13260
tcccgcattt ggtacagcgc agtaaccggc aaaatcgcgc cgaaggatgt cgctgccgac    13320
tgggcaatgg agcgcctgcc ggcccagtat cagcccgtca tacttgaagc taggcaggct    13380
tatcttggac aagaagatcg cttggcctcg cgcgcagatc agttggaaga atttgttcac    13440
tacgtgaaag gcgagatcac caaggtagtc ggcaaataat gtctaacaat tcgttcaagc    13500
cgacgccgct tcgcggcgcg gcttaactca agcgttagat gctgcaggca tcgtggtgtc    13560
acgctcgtcg tttggtatgg cttcattcag ctccggttcc caacgatcaa ggcgagttac    13620
atgatccccc atgttgtgca aaaaagcggt tagctccttc ggtcctccga tcg           13673

<210> SEQ ID NO 2
<211> LENGTH: 15584
<212> TYPE: DNA
<213> ORGANISM: Artificial Sequence
<220> FEATURE:
<221> NAME/KEY: misc_feature
<222> LOCATION: (1)..(15584)
<223> OTHER INFORMATION: Synthetic Plasmid DNA Molecule

<400> SEQUENCE: 2 aggattttc ggcgctgcgc tacgtccgcg accgcgttga gggatcaagc cacagcagcc      60
cactcgacct tctagccgac ccagacgagc caagggatct ttttggaatg ctgctccgtc    120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240
ttcacgccct tttaaatatc cgattattct aataaacgct cttttctctt aggtttaccc    300
gccaatatat cctgtcaaac actgatagtt taaactgaag gcgggaaacg acaatctgat    360
ccccatcaag cttgatctcg tcaatttttc ccttttgtaa ttttgtaatt tataatttac    420
tttcctgtat gcttctaact ctgtcgtttt aaaattttaa taaaatttca gtaggggctt    480 gccctcctg tcctataaaa aaaagttgac gtgaatagat ttcattaaga ggttggatgt    540
tagtgggatg acatgactat tagtaggacg agatgatgtg gaaagttagt gggagatgat    600
atggatagtt tttgctttca tcgaaaggtt ggaagttagt atgatgacat ggctaatata    660
gatacataga tatagactac caacatggct gcatgccccc aagctctccc actatatata    720
tctctggtag cacatcatcc caattcacaa tgcttacaaa aacccatcca tcatttagc    780 tgttgataca aaagagctcg aagggagatc taccgtcttc ggtacgcgct cactccgccc    840
tctgcctttg ttactgccac gtttctctga atgctctctt gtgtggtgat tgctgagagt    900
```

```
ggtttagctg atctagaat tacactctga aatcgtgttc tgcctgtgct gattacttgc    960
cgtcctttgt agcagcaaaa tagggaca tggtagtacg aaacgaagat agaacctaca   1020
cagcaatacg agaaatgtgt aatttggtgc ttagcggtat ttatttaagc acatgttggt   1080
gttatagggc acttggattc agaagtttgc tgttaattta ggcacaggct tcatactaca   1140
tgggtcaata gtatagggat tcatattata ggcgatacta taataatttg ttcgtctgca   1200
gagcttatta tttgccaaaa ttagatattc ctattctgtt tttgtttgtg tgctgttaaa   1260
ttgttgatcc cgatttggca agtgttccag agcaaaagct ggaagctctc gtagtctgag   1320
cctctttgct gattcataca agttatgacc atctacatgg atcgtctcac caagaaattt   1380
gtagactgca ggattttttcc ctgaccggag tgcaccagct gggttccaac tgaatttata   1440
ggcaagcgga ttgtttgctg cagctggaga tggcaatcca ccacagtaag atgtaaatgc   1500
ctttattttt cccttcgtg catgagcttc atcaatcatc ttcattgaca tcaagtgatc   1560
tatgccagga tctaggccca tttcacaaag tatagttaca cctgcatctt tggcagcttg   1620
gctcaagttt gacatggatt catcaacata gcttgccgtt accatgtgct tcttcaactc   1680
tatgcatact cctgcaatgg cagcatgaaa actagcaggc agcaagctaa ttacaacctc   1740
aacctgagaa acaagatctg aaaggcttcc aatatcagca acatcaagct gggtagcagt   1800
tgtattttca ataccatcaa ctgtctcttc tgcatctttt tgatacaaag atgccacgat   1860
aacatgaatt tgatctgcat catggtcatc aacaccatag gtacatatgt ctgggtaaga   1920
tgccagaaac tcagcagctg gccgacagac tcttccagct ccaaaccggt gctgcctgct   1980
agttttcatg ctgccattgc aggagtatgc atagagttga agaagcacat ggtaacggca   2040
agctatgttg atgaatccat gtcaaacttg agccaagctg ccaaagatgc aggtgtaact   2100
atactttgtg aaatgggcct agatcctggc atagatcact tgatgtcaat gaagatgatt   2160
gatgaagctc atgcacgaaa gggaaaaata aaggcattta catcttactg tggtggattg   2220
ccatctccag ctgcagcaaa caatccgctt gcctataaat tcagttggaa cccagctggt   2280
gcactccggt cagggaaaaa tcctgcagtc tacaaatttc ttggtgagac gatccatgta   2340
gatggtcata acttgtatga atcagcaaag aggctcagac tacgagagct tccagctttt   2400
gctctggaac acttgccaaa tcggaattaa cgcctgaagg aataaatata aatgacgaaa   2460
ttttgatgtt tatctctgct cctttattgt gaccataagt caagatcaga tgcacttgtt   2520
ttaaatattg ttgtctgaag aaataagtac tgacagtatt ttgatgcatt gatctgcttg   2580
tttgttgtaa caaatttaa aaataaagag tttccttttt gttgctctcc ttacctcctg   2640
atggtatcta gtatctacca actgacacta tattgcttct cttacatac gtatcttgct   2700 cgatgccttc tccctagtgt tgaccagtgt tactcacata gtctttgctc atttcattgt   2760
aatgcagata ccaagcggat ccatggtttc gccgacgaat ctcctcccgg cgcggaagat   2820 caccctgtc tcaaatggcg gcgcagcgac ggcgagcccc tcttctccct cggtggccgc   2880
acggccacgg cgactccctt caggcctcca atctgtgact ggtagaggga aggtttcctt   2940
ggcagccatc actagcacag gtttaacagc taagaccgga gtagagcact tggcaccgt   3000 gggagtagca atggtaactc cattcacgga aagtggagac atcgatatag ctgctggccg   3060
cgaggtcgcg gcttatctag tcgataaagg cttggattct ttggtgctcg cgggcaccac   3120
tggtgaatcc ccaacgacaa ccgccgctga gaaactagaa ctgctcaagg ccgtgcgtga   3180
ggaagtaggg gataggcga aactaatcgc cggtgtcgga accaataaca cgcggacatc   3240
tgtggaactt gcggaggctg ctgcttctgc tggcgcagac ggcctttag tcgtaactcc   3300
```

```
ttattacagt aagccgagcc aggagggatt gctggcgcac ttcggggcaa tcgcagcagc   3360
aacagaggtg ccaatttgcc tctacgacat tcctggtagg tcaggtattc caattgagtc   3420
tgataccatg agacgcctga gtgaattacc tacgattttg gcggtcaaag acgccaaagg   3480
ggacctggtt gcagccacgt cattgatcaa agaaacggga cttgcctggt attcaggcga   3540
tgacccacta aaccttgttt ggcttgcttt gggcggatca ggttttatat ccgtaattgg   3600
acatgcagcc cccacagcat taagggagtt gtacacaagt ttcgaggaag cgacctggt   3660 ccgtgcgagg gagatcaacg ccaaactatc accgctggta gctgcccagg gtcgcttggg   3720
tggagtcagc ttggcaaaag ctgctctgcg tctgcaaggc atcaacgtag agatcctag   3780 gcttccaata atggctccaa atgagcagga acttgaggct ctgcgagaag acatgaaaaa   3840
agctggagtt ctataagaat tctgcatgcg tttggacgta tgctcattca ggttggagcc   3900
aatttggttg atgtgtgtgc gagttcttgc gagtctgatg agacatctct gtattgtgtt   3960
tctttcccca gtgttttctg tacttgtgta atcggctaat cgccaacaga ttcggcgatg   4020
aataaatgag aaataaattg ttctgatttt gagtgcaaaa aaaaggaat tgattcgagt   4080 ggcggccgcg ttttatgaat aataataatg catatctgtg cattactacc tgggatacaa   4140
gggcttctcc gccataacaa attgagttgc gatgctgaga acgaacgggg aagaaagtaa   4200
gcgccgccca aaaaaacga acatgtacgt cggctatagc aggtgaaagt tcgtgcgcca   4260
atgaaaaggg aacgatatgc gttgggtagt tgggatactt aaatttggag agtttgttgc   4320
atacactaat ccactaaagt tgtctatctt tttaacagct ctaggcagga tataagattt   4380
atatctaatc tgttggagtt gcttttagag taacttttct ctctgtttcg tttatagccg   4440
attagcacaa aattaaacta ggtgacgaga aataaagaaa aacggaggca gtaaaaaata   4500
cccaaaaaaa tacttggaga tttttgtctc aaaattatct tctaattta aaagctacat   4560 attaaaaata ctatatatta aaaatacttc gagatcattg cttgggatgg gcagggccaa   4620
tagctaattg ctaaggatgg gctatatta tgtatcgtct gaaacatgta ggggctaata   4680
gttagatgac taatttgctg tgttcgtacg gggtgctgtt tgagcctagc gatgaagggt   4740
catagtttca tacaagaact cacttttggt tcgtctgctg tgtctgttct cagcgtaacg   4800
gcatcaatgg atgccaaact ccgcaagggg acaaatgaag aagcgaagag attatagaac   4860
acgcacgtgt cattatttat ttatggactt gcctcagtag cttacagcat cgtacccgca   4920
cgtacatact acagagccac acttattgca ctgcctgccg cttacgtaca tagttaacac   4980
gcagagaggt atatacatac acgtccaacg tctccactca ggctcatgct acgtacgcac   5040
gtcggtcgcg cgccaccctc tcgttgcttc ctgctcgttt tggcgaattc tagaaggatc   5100
ataccgaaag aaaggcctct ctattgatgt actcttgttg ataaattcaa tggaacctcc   5160
aatatcacaa gttatgtcac aaacgccgac taaaggacaa ccagtctcca tcaattgctg   5220
taactgatcc atatttagta atggtggaaa cctcttctcc caatacatac agtttacgat   5280
gacagatgca tatggagcaa ttctttcatg aaaaacaggg gtgtagtgtt ctggatgagc   5340
ataatagtca cctttgtcaa attgtctggt gggatccttg tgagaaacca tgtctctaga   5400
ggtcacaaca caaccataaa gttgaaatac tctcttggtc gactgagatt gcttagacag   5460
attcctggcc tgaaaccggt aggctgcagt cattgtcgtt gcagaagaga tagcaacatt   5520
tggacttcca tccggaattt gtccgatagt gtttgtgttc actggagttg gaaacgtctc   5580
tcagggtgcg caggagatat tcaagttatt gccccatacc tttgttgatg ctgagaagct   5640
tcccgaaatt tttcaggcca ggaatctgtc taagcaatct cagtcgacca agagagtatt   5700
```

```
tcaactttat ggttgtgttg tgacctctag agacatggtt tctcacaagg atcccaccag    5760
acaatttgac aaaggtgact attatgctca tccagaacac tacaccctg ttttcatga    5820 aagaattgct ccatatgcat ctgtcatcgt aaactgtatg tattgggaga agaggttcc    5880 accattacta aatatggatc agttacagca attgatggag actggttgtc ctttagtcgg    5940
cgtttgtgac ataacttgtg atattggagg ttccattgaa tttatcaaca agagtacatc    6000
aatagagagg cctttctttc ggtatgatcc ttctaagatc cgcaggatct ggtaggctag    6060
cagagcgagc tagataccc acgtgcgcac gctgcccaga gatcctgccg ctgccgctgc    6120
cgctgatgct tgagctacga ctacgagtga ggtagatgag ggcgagggag agctgggtgt    6180
ttatagaggg cgtggcaacg cgcggaggcg ggatctggcg cggccgcgtg ggacgcatgc    6240
gggactcgtg tcgggggcag cgcgacacct gtgtagggg tgtcgaggac aaggcttcct    6300
cggtcgcgcc gcttccgcgc ggcgatatat acgaggttgt gtgtgtgcgc gcactgccgt    6360
tggatcggcc gctggttgcc ggaggtggcg gggccgaatc tcatgtgggc cgtagtccgg    6420
gcctctttta cttcttttgt cttccgtgtc tcactatttt ctggtccacg tagacctaca    6480
tcacatacta gcaagaacta gtaaaagcat ctgagcgtca gtagtttt agtatattaa    6540 taataatata gatttattgt gactaaaata taattgtgg aaacaatgtg cttggtacct    6600
gttgagattt tgtgaagaac tacagcatga caacatattt aaattgagga cacttcctct    6660
cttctccgaa gaggatgaat ggtagggtgt ccagaaaaca aatttgtata tcgaaactca    6720
tgagaagtta cgaagcgtaa aatatggatt atcgtaatta tttgctgaag gtgagatgca    6780
tgttctctca atcgattaac cgtgtaatgc tcattgccaa taataatatc ctagggaaag    6840
actcgatata tgatgaaaga caagacaaca ataatcttcg ccatcttata cctttggagg    6900
ttctctaaac aggggtaca cgggcgtagg gatacaggaa tgccaatccc gatagcagat    6960
atatttgagg tgtttggttt gaggaatgag atagtcaatc atcttctcac tcctcaaatt    7020 tttgttggt ttgtggaatg gagtgagtta attcatcatc acctcattcc tcaaagttag    7080
ttgcttagtg acctcgagca tgcatctagt agcttgttaa cgcggccgca tcgatcgtga    7140
agtttctcat ctaagccccc atttggacgt gaatgtagac acgtcgaaat aaagatttcc    7200
gaattagaat aatttgttta ttgctttcgc ctataaatac gacggatcgt aatttgtcgt    7260
tttatcaaaa tgtactttca ttttataata acgctgcgga catctacatt tttgaattga    7320
aaaaaaattg gtaattactc tttcttttc tccatattga ccatcatact cattgctgat    7380
ccatgtagat ttcccggaca tgaagccatt tacaattgaa tatatcctgc cgccgctgcc    7440
gctttgcacc cggtggagct tgcatgttgg tttctacgca gaactgagcc ggttaggcag    7500
ataatttcca ttgagaactg agccatgtgc accttccccc caacacggtg agcgacgggg    7560
caacggagtg atccacatgg gacttttgta cactcgaggt cattcatatg cttgagaaga    7620
gagtcgggat agtccaaaat aaaacaaagg taagattacc tggtcaaaag tgaaaacatc    7680
agttaaaagg tggtataaag taaaatatcg gtaataaaag gtggcccaaa gtgaaattta    7740
ctcttttcta ctattataaa aattgaggat gttttgtcg gtactttgat acgtcatttt    7800
tgtatgaatt ggttttaag tttattcgct tttggaaatg catatctgta tttgagtcgg    7860
gttttaagtt cgtttgcttt tgtaaataca gagggatttg tataagaaat atctttagaa    7920
aaacccatat gctaatttga cataattttt gagaaaaata tatattcagg cgaattctca    7980
caatgaacaa taataagatt aaaatagctt tcccccgttg cagcgcatgg gtatttttc    8040 tagtaaaaat aaaagataaa cttagactca aaacatttac aaaaacaacc cctaaagttc    8100
```

```
ctaaagccca aagtgctatc cacgatccat agcaagccca gcccaaccca acccaaccca   8160
acccacccca gtccagccaa ctggacaata gtctccacac ccccccacta tcaccgtgag   8220
ttgtccgcac gcaccgcacg tctcgcagcc aaaaaaaaaa agaaagaaaa aaaagaaaaa   8280
gaaaaaacag caggtgggtc cgggtcgtgg gggccggaaa cgcgaggagg atcgcgagcc   8340
agcgacgagg ccggccctcc ctccgcttcc aaagaaacgc cccccatcgc cactatatac   8400
atacccccc ctctcctccc atcccccaa ccctaccacc accaccacca ccacctccac   8460
ctcctccccc ctcgctgccg gacgacgagc tcctccccc tcccctccg ccgccgccgc   8520
gccggtaacc accccgcccc tctcctcttt ctttctccgt ttttttttcc gtctcggtct   8580
cgatctttgg ccttggtagt ttgggtgggc gagaggcggc ttcgtgcgcg cccagatcgg   8640
tgcgcgggag gggcgggatc tcgcggctgg ggctctcgcc ggcgtggatc cggcccggat   8700
ctcgcgggga atggggctct cggatgtaga tctgcgatcc gccgttgttg ggggagatga   8760
tggggggttt aaaatttccg ccgtgctaaa caagatcagg aagaggggaa aagggcacta   8820
tggtttatat ttttatatat ttctgctgct tcgtcaggct tagatgtgct agatctttct   8880
ttcttctttt tgtgggtaga atttgaatcc ctcagcattg ttcatcggta gttttcttt   8940
tcatgatttg tgacaaatgc agcctcgtgc ggagcttttt tgtaggtaga agtgatcaac   9000
catggcgcaa gttagcagaa tctgcaatgg tgtgcagaac ccatctctta tctccaatct   9060
ctcgaaatcc agtcaacgca aatctccctt atcggtttct ctgaagacgc agcagcatcc   9120
acgagcttat ccgatttcgt cgtcgtgggg attgaagaag agtgggatga cgttaattgg   9180
ctctgagctt cgtcctctta aggtcatgtc ttctgtttcc acggcgtgca tgcttcacgg   9240
tgcaagcagc cggcccgcaa ccgcccgcaa atcctctggc cttccggaa ccgtccgcat   9300
tcccggcgac aagtcgatct cccaccggtc cttcatgttc ggcggtctcg cgagcggtga   9360
aacgcgcatc accggccttc tggaaggcga ggacgtcatc aatacgggca aggccatgca   9420
ggcgatgggc gcccgcatcc gtaaggaagg cgacacctgg atcatcgatg cgtcggcaa   9480
tggcggcctc ctggcgcctg aggcgccgct cgatttcggc aatgccgcca cgggctgccg   9540
cctgacgatg ggcctcgtcg gggtctacga tttcgcagc accttcatcg cgacgcctc   9600
gctcacaaag cgcccgatgg gccgcgtgtt gaacccgctg cgcgaaatgg gcgtgcaggt   9660
gaaatcggaa gacggtgacc gtcttcccgt taccttgcgc gggccgaaga cgccgacgcc   9720
gatcacctac cgcgtgccga tggcctccgc acaggtgaag tccgccgtgc tgctcgccgg   9780
cctcaacacg cccggcatca cgacggtcat cgagccgatc atgacgcgcg atcatacgga   9840
aaagatgctg cagggcttg gcgccaacct taccgtcgag acggatgcgg acggcgtgcg   9900
caccatccgc ctggaaggcc gcggcaagct caccggccaa gtcatcgacg tgccgggcga   9960
cccgtcctcg acggccttcc cgctggttgc ggccctgctt gttccgggct ccgacgtcac  10020
catcctcaac gtgctgatga cccccaccg caccggcctc atcctgacgc tgcaggaaat  10080
gggcgccgac atcgaagtca tcaacccgcg ccttgccggc ggcgaagacg tggcggacct  10140
gcgcgttcgc tcctccacgc tgaagggcgt cacggtgccg aagaccgcg cgccttcgat  10200
gatcgacgaa tatccgattc tcgctgtcgc cgccgcttc gcggaagggg cgaccgtgat  10260
gaacggtctg gaagaactcc gcgtcaagga aagcgaccgc ctctcggccg tcgccaatgg  10320
cctcaagctc aatggcgtgg attgcgatga gggcgagacg tcgctcgtcg tgcgtggccg  10380
ccctgacgga aaggggctcg gcaacgcctc gggcgccgcc gtcgcaccc atctcgatca  10440
ccgcatcgcc atgagcttcc tcgtcatggg cctcgtgtcg gaaaaccctg tcacggtgga  10500
```

```
cgatgccacg atgatcgcca cgagcttccc ggagttcatg gacctgatgg ccgggctggg    10560
cgcgaagatc gaactctccg atacgaaggc tgcctgatga gctcgaattc ccgatcgttc    10620
aaacatttgg caataaagtt tcttaagatt gaatcctgtt gccggtcttg cgatgattat    10680
catataattt ctgttgaatt acgttaagca tgtaataatt aacatgtaat gcatgacgtt    10740
atttatgaga tgggttttta tgattagagt cccgcaatta tacatttaat acgcgataga    10800
aaacaaaata tagcgcgcaa actaggataa attatcgcgc gcggtgtcat ctatgttact    10860
agatcgggga tgggggatct cagcccctgg ggggatggga ggcccgcgtt agcgggccgg    10920
gagggttcga aaggggggg cacccccctt cggcgtgcgc ggtcacgcgc acagggcgca    10980
gccctggtta aaaacaaggt ttataaatat tggtttaaaa gcaggttaaa agacaggtta    11040
gcggtggccg aaaaacgggc ggaaacccctt gcaaatgctg gattttctgc ctgtggacag    11100
cccctcaaat gtcaataggt gcgcccctca tctgtcagca ctctgcccct caagtgtcaa    11160
ggatcgcgcc cctcatctgt cagtagtcgc gcccctcaag tgtcaatacc gcagggcact    11220
tatccccagg cttgtccaca tcatctgtgg gaaactcgcg taaaatcagg cgttttcgcc    11280
gatttgcgag gctggccagc tccacgtcgc cggccgaaat cgagcctgcc cctcatctgt    11340
caacgccgcg ccgggtgagt cggcccctca agtgtcaacg tccgcccctc atctgtcagt    11400
gagggccaag ttttccgcga ggtatccaca acgccggcgg ccggccgcgg tgtctcgcac    11460
acggcttcga cggcgtttct ggcgcgtttg cagggccata gacggccgcc agcccagcgg    11520
cgagggcaac cagcccggtg agcgtcggaa agggtcgatc gaccgatgcc cttgagagcc    11580
ttcaacccag tcagctcctt ccggtgggcg cggggcatga ctatcgtcgc cgcacttatg    11640
actgtcttct ttatcatgca actcgtagga caggtgccgg cagcgctctg ggtcattttc    11700
ggcgaggacc gctttcgctg gagcgcgacg atgatcggcc tgtcgcttgc ggtattcgga    11760
atcttgcacg ccctcgctca agccttcgtc actggtcccg ccaccaaacg tttcggcgag    11820
aagcaggcca ttatcgccgg catggcggcc gacgcgctgg gctacgtctt gctggcgttc    11880
gcgacgcgag gctggatggc cttccccatt atgattcttc tcgcttccgg cggcatcggg    11940
atgcccgcgt tgcaggccat gctgtccagg caggtagatg acgaccatca gggacagctt    12000
caaggatcgc tcgcggctct taccagccta acttcgatca ttggaccgct gatcgtcacg    12060
gcgatttatg ccgcctcggc gagcacatgg aacgggttgg catggattgt aggcgccgcc    12120
ctataccttg tctgcctccc cgcgttgcgt cgcggtgcat ggagccgggc cacctcgacc    12180
tgaatggaag ccggcggcac ctcgctaacg gattcaccac tccaagaatt ggagccaatc    12240
aattcttgcg gagaactgtg aatgcgcaaa ccaacccttg gcagaacata tccatcgcgt    12300
ccgccatctc cagcagccgc acgcggcgca tctcgggcag cgttgggtcc tggccacggg    12360
tgcgcatgat cgtgctcctg tcgttgagga cccggctagg ctggcggggt tgccttactg    12420
gttagcagaa tgaatcaccg atacgcgagc gaacgtgaag cgactgctgc tgcaaaacgt    12480
ctgcgacctg agcaacaaca tgaatggtct tcggtttccg tgtttcgtaa agtctggaaa    12540
cgcggaagtc agcgccctgc accattatgt tccggatctg catcgcagga tgctgctggc    12600
taccctgtgg aacacctaca tctgtattaa cgaagcgctg gcattgaccc tgagtgattt    12660
ttctctggtc ccgccgcatc cataccgcca gttgtttacc ctcacaacgt tccagtaacc    12720
gggcatgttc atcatcagta acccgtatcg tgagcatcct ctctcgtttc atcggtatca    12780 ttaccccat gaacagaaat cccccttaca cggaggcatc agtgaccaaa caggaaaaaa    12840
ccgcccttaa catggcccgc tttatcagaa gccagacatt aacgcttctg gagaaactca    12900
```

```
acgagctgga cgcggatgaa caggcagaca tctgtgaatc gcttcacgac cacgctgatg  12960
agctttaccg cagctgcctc gcgcgtttcg gtgatgacgg tgaaaacctc tgacacatgc  13020
agctcccgga cacggtcaca gcttgtctgt aagcggatgc cgggagcaga caagcccgtc  13080
agggcgcgtc agcgggtgtt ggcggtgtc ggggcgcagc catgacccag tcacgtagcg  13140
atagcggagt gtatactggc ttaactatgc ggcatcagag cagattgtac tgagagtgca  13200
ccatatgcgg tgtgaaatac cgcacagatg cgtaaggaga aaataccgca tcaggcgctc  13260
ttccgcttcc tcgctcactg actcgctgcg ctcggtcgtt cggctgcggc gagcggtatc  13320
agctcactca aaggcggtaa tacgttatcc acagaatca ggggataacg caggaaagaa  13380
catgtgagca aaaggccagc aaaaggccag gaaccgtaaa aaggccgcgt tgctggcgtt  13440
tttccatagg ctccgccccc ctgacgagca tcacaaaaat cgacgctcaa gtcagaggtg  13500
gcgaaacccg acaggactat aaagatacca ggcgtttccc cctggaagct ccctcgtgcg  13560
ctctcctgtt ccgaccctgc cgcttaccgg atacctgtcc gcctttctcc cttcgggaag  13620
cgtggcgctt tctcatagct cacgctgtag gtatctcagt tcggtgtagg tcgttcgctc  13680
caagctgggc tgtgtgcacg aaccccccgt tcagcccgac cgctgcgcct tatccggtaa  13740
ctatcgtctt gagtccaacc cggtaagaca cgacttatcg ccactggcag cagccactgg  13800
taacaggatt agcagagcga ggtatgtagg cggtgctaca gagttcttga agtggtggcc  13860
taactacggc tacactagaa ggacagtatt tggtatctgc gctctgctga gccagttac  13920 cttcggaaaa agagttggta gctcttgatc cggcaaacaa accaccgctg gtagcggtgg  13980
tttttttgtt tgcaagcagc agattacgcg cagaaaaaaa ggatctcaag aagatccttt  14040
gatcttttct acggggtctg acgctcagtg gaacgaaaac tcacgttaag ggattttggt  14100
catgagatta tcaaaaagga tcttcaccta gatccttta aattaaaaat gaagttttaa  14160
atcaatctaa agtatatatg agtaaacttg gtctgacagt taccaatgct taatcagtga  14220
ggcacctatc tcagcgatct gtctatttcg ttcatccata gttgcctgac tccccgtcgt  14280
gtagataact acgatacggg agggcttacc atctggcccc agtgctgcaa tgataccgcg  14340
agacccacgc tcaccggctc cagatttatc agcaataaac cagccagccg aagggccga  14400 gcgcagaagt ggtcctgcaa ctttatccgc ctccatccag tctattaatt gttgccggga  14460
agctagagta agtagttcgc cagttaatag tttgcgcaac gttgttgcca ttgctgcagg  14520
tcgggagcac aggatgacgc ctaacaattc attcaagccg acaccgcttc gcggcgcggc  14580
ttaattcagc agttaaacat catgagggaa gcggtgatcg ccgaagtatc gactcaacta  14640
tcagaggtag ttggcgtcat cgagcgccat ctcgaaccga cgttgctggc cgtacatttg  14700
tacggctccg cagtggatgg cggcctgaag ccacacagtg atattgattt gctggttacg  14760
gtgaccgtaa ggcttgatga aacaacgcgg cgagctttga tcaacgacct tttggaaact  14820
tcggcttccc ctggagagag cgagattctc cgcgctgtag aagtcaccat tgttgtgcac  14880
gacgacatca ttccgtggcg ttatccagct aagcgcgaac tgcaatttgg agaatggcag  14940
cgcaatgaca ttcttgcagg tatcttcgag ccagccacga tcgacattga tctggctatc  15000
ttgctgacaa agcaagaga acatagcgtt gccttggtag tccagcggc ggaggaactc  15060 tttgatccgg ttcctgaaca ggatctattt gaggcgctaa atgaaacctt aacgctatgg  15120
aactcgccgc ccgactgggc tggcgatgag cgaaatgtag tgcttacgtt gtcccgcatt  15180
tggtacagcg cagtaaccgg caaaatcgcg ccgaaggatg tcgctgccga ctgggcaatg  15240
gagcgcctgc cggcccagta tcagcccgtc atacttgaag ctaggcaggc ttatcttgga  15300
```

```
caagaagatc gcttggcctc gcgcgcagat cagttggaag aatttgttca ctacgtgaaa   15360
ggcgagatca ccaaggtagt cggcaaataa tgtctaacaa ttcgttcaag ccgacgccgc   15420
ttcgcggcgc ggcttaactc aagcgttaga tgctgcaggc atcgtggtgt cacgctcgtc   15480
gtttggtatg gcttcattca gctccggttc ccaacgatca aggcgagtta catgatcccc   15540
catgttgtgc aaaaaagcgg ttagctcctt cggtcctccg atcg                   15584
```